US010806852B2

(12) United States Patent
Schulte et al.

(10) Patent No.: US 10,806,852 B2
(45) Date of Patent: Oct. 20, 2020

(54) SYSTEM FOR SYRINGE ENGAGEMENT TO AN INJECTOR

(71) Applicant: BAYER HEALTHCARE LLC, Whippany, NJ (US)

(72) Inventors: Stephen Schulte, Gibsonia, PA (US); Christopher L. Swenglish, Connellsville, PA (US); Luis Castillo, Oviedo, FL (US); Charles A. Lang, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 920 days.

(21) Appl. No.: 15/126,598

(22) PCT Filed: Mar. 18, 2015

(86) PCT No.: PCT/US2015/021171
§ 371 (c)(1),
(2) Date: Sep. 16, 2016

(87) PCT Pub. No.: WO2015/142995
PCT Pub. Date: Sep. 24, 2015

(65) Prior Publication Data
US 2017/0080148 A1 Mar. 23, 2017

Related U.S. Application Data

(60) Provisional application No. 61/970,018, filed on Mar. 25, 2014, provisional application No. 61/955,527, filed on Mar. 19, 2014.

(51) Int. Cl.
*A61M 5/145* (2006.01)
*A61M 5/00* (2006.01)

(52) U.S. Cl.
CPC .......... *A61M 5/1458* (2013.01); *A61M 5/007* (2013.01); *A61M 5/1456* (2013.01);
(Continued)

(58) Field of Classification Search
CPC ............ A61M 5/14566; A61M 5/1458; A61M 5/146; A61M 5/14546; A61M 5/007;
(Continued)

(56) References Cited

U.S. PATENT DOCUMENTS 1,265,537 A 5/1918 Ivan
1,687,323 A 10/1928 Cook
(Continued)

FOREIGN PATENT DOCUMENTS

AU 317487 1/2008
DE 2919978 A1 11/1980
(Continued)

OTHER PUBLICATIONS

"International Preliminary Report on Patentability from Corresponding PCT Application No. PCT/US2015/021171", dated Sep. 20, 2016.
(Continued)

*Primary Examiner* — William R Carpenter
*Assistant Examiner* — Hamza A Darb
(74) *Attorney, Agent, or Firm* — David Schramm; Joseph L. Kent; James R. Stevenson

(57) ABSTRACT

An injector system for injecting fluid includes a syringe and an injector. The syringe includes a body and a plunger movably disposed within the body. The plunger has at least one flexible leg extending toward the rearward end of the body. The injector has a housing with a front plate, a drive member at least partially disposed within the housing and operable to engage the plunger, and a syringe release assembly operable to release the syringe. The syringe assembly
(Continued)

includes a syringe release gear that forms an enclosure for receiving the syringe when the syringe is fully seated within the housing and a plunger release tube surrounding at least a portion of the drive member. The plunger release tube has a first end rotationally engaged with the syringe release gear. Rotation of the syringe release assembly releases the at least one flexible leg from the drive member.

17 Claims, 13 Drawing Sheets

(52) U.S. Cl.
CPC .... *A61M 5/14546* (2013.01); *A61M 5/14566* (2013.01); *A61M 2205/3306* (2013.01); *A61M 2205/581* (2013.01)

(58) Field of Classification Search
CPC .... A61M 2205/581; A61M 2205/3306; A61M 5/1452; A61M 2005/14573
See application file for complete search history.

(56) References Cited

U.S. PATENT DOCUMENTS

| | | |
|---|---|---|
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Porat |
| 3,270,483 A | 9/1966 | Smoyer et al. |
| 3,348,545 A | 10/1967 | Sarnoff et al. |
| 3,468,471 A | 9/1969 | Linder |
| 3,604,417 A | 9/1971 | Stolzenberg et al. |
| 3,623,474 A | 11/1971 | Heilman |
| 3,645,262 A | 2/1972 | Harrigan |
| 3,701,345 A | 10/1972 | Heilman |
| 3,705,582 A | 12/1972 | Stumpf et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wootten et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,144,885 A | 3/1979 | Stait |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,791,290 A | 12/1988 | Noone et al. |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,945,363 A | 7/1990 | Hoffman |
| 4,946,009 A | 8/1990 | Knutson |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |

(56) References Cited

U.S. PATENT DOCUMENTS

| | | |
|---|---|---|
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| D364,461 S | 11/1995 | Liebert et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,795,337 A | 8/1998 | Grimard |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| D403,762 S | 1/1999 | Gabbard et al. |
| 5,865,805 A | 2/1999 | Ziemba |
| 5,873,861 A | 2/1999 | Hitchins et al. |
| D407,362 S | 3/1999 | Schardt |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,919,167 A | 7/1999 | Mulhauser et al. |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,300 A | 12/1999 | Butcher et al. |
| 6,017,330 A | 1/2000 | Hitchins et al. |
| 6,042,565 A | 3/2000 | Hirschman et al. |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,162,200 A | 12/2000 | Sawa et al. |
| 6,196,999 B1 | 3/2001 | Goethel et al. |
| 6,221,045 B1 | 4/2001 | Duchon et al. |
| 6,224,577 B1 | 5/2001 | Dedola et al. |
| 6,267,749 B1 | 7/2001 | Miklos et al. |
| 6,312,410 B1 | 11/2001 | Yamamoto |
| 6,315,758 B1 | 11/2001 | Neer et al. |
| 6,322,535 B1 | 11/2001 | Hitchins et al. |
| RE37,487 E | 12/2001 | Reilly et al. |
| 6,332,877 B1 | 12/2001 | Michels |
| 6,336,913 B1 | 1/2002 | Spohn et al. |
| 6,339,718 B1 | 1/2002 | Zatezalo et al. |
| 6,345,262 B1 | 2/2002 | Madden |
| 6,368,307 B1 | 4/2002 | Ziemba et al. |
| 6,432,089 B1 | 8/2002 | Kakimi et al. |
| 6,447,487 B1 | 9/2002 | Cane' |
| 6,511,459 B1 | 1/2003 | Fago |
| 6,517,516 B1 | 2/2003 | Caizza |
| 6,533,758 B1 | 3/2003 | Staats et al. |
| 6,569,127 B1 | 5/2003 | Fago et al. |
| 6,582,399 B1 | 6/2003 | Smith et al. |
| 6,585,700 B1 | 7/2003 | Trocki et al. |
| 6,652,489 B2 | 11/2003 | Trocki et al. |
| 6,659,979 B2 | 12/2003 | Neer et al. |
| 6,669,663 B1 | 12/2003 | Thompson |
| 6,676,635 B2 | 1/2004 | Nemoto |
| 6,733,477 B2 | 5/2004 | Cowan et al. |
| 6,733,478 B2 | 5/2004 | Reilly et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,025,757 B2 | 4/2006 | Reilly et al. |
| 7,029,459 B2 | 4/2006 | Reilly |
| 7,240,882 B2 | 7/2007 | Degentesh et al. |
| 7,264,612 B2 | 9/2007 | Nemoto |
| D555,802 S | 11/2007 | Coulling et al. |

(56) References Cited

U.S. PATENT DOCUMENTS

| | | |
|---|---|---|
| 7,300,417 B1 | 11/2007 | Goethel et al. |
| 7,337,538 B2 | 3/2008 | Moutafis et al. |
| 7,344,520 B2 | 3/2008 | Nemoto |
| 7,393,341 B2 | 7/2008 | Nemoto |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,503,906 B2 | 3/2009 | Nemoto |
| 7,540,856 B2 | 6/2009 | Trocki et al. |
| 7,553,294 B2 | 6/2009 | Lazzaro et al. |
| 7,566,326 B2 | 7/2009 | Duchon et al. |
| 7,666,169 B2 | 2/2010 | Cowan et al. |
| 7,682,345 B2 | 3/2010 | Savage |
| 7,695,457 B2 | 4/2010 | Nemoto |
| 7,803,134 B2 | 9/2010 | Sharifi et al. |
| 7,854,726 B2 | 12/2010 | Fago et al. |
| 7,875,005 B2 | 1/2011 | Nemoto |
| D632,389 S | 2/2011 | Maeda et al. |
| D637,492 S | 5/2011 | Baird et al. |
| 7,972,306 B2 | 7/2011 | Shearn |
| 7,998,133 B2 | 8/2011 | Fago et al. |
| 8,012,124 B1 | 9/2011 | Fago et al. |
| 8,012,125 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,133,203 B2 | 3/2012 | Hack |
| 8,172,814 B2 | 5/2012 | Cane |
| 8,177,757 B2 | 5/2012 | Nemoto et al. |
| D665,498 S | 8/2012 | Tamura et al. |
| 8,262,644 B2 | 9/2012 | Fago et al. |
| 8,308,689 B2 | 11/2012 | Lewis |
| 8,353,879 B2 | 1/2013 | Goethel et al. |
| 8,454,560 B2 | 6/2013 | Strobl |
| D686,322 S | 7/2013 | Maeda et al. |
| 8,475,415 B2 | 7/2013 | Schiller et al. |
| 8,480,631 B2 | 7/2013 | Wotton et al. |
| 8,574,200 B2 | 11/2013 | Hack |
| 8,585,658 B2 | 11/2013 | Forstreuter |
| 8,597,246 B1 | 12/2013 | Fago et al. |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |
| 8,845,596 B2 | 9/2014 | Berman et al. |
| 8,851,866 B2 | 10/2014 | Moutafis et al. |
| 8,857,674 B2 | 10/2014 | Nighy et al. |
| 8,864,712 B1 | 10/2014 | Fago et al. |
| 8,926,569 B2 | 1/2015 | Bisegna et al. |
| 8,932,255 B1 | 1/2015 | Fago et al. |
| 9,173,995 B1 | 11/2015 | Tucker et al. |
| 9,174,003 B2 | 11/2015 | Cowan et al. |
| 9,199,033 B1 | 12/2015 | Cowan et al. |
| 9,474,857 B2 | 10/2016 | Riley et al. |
| 9,694,131 B2 | 7/2017 | Cowan et al. |
| 9,844,622 B2 | 12/2017 | Savage et al. |
| 2002/0165491 A1* | 11/2002 | Reilly .............. A61M 5/14546 604/154 |
| 2003/0004468 A1 | 1/2003 | Righi et al. |
| 2003/0009133 A1 | 1/2003 | Ramey |
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0074453 A1 | 4/2004 | Roelle et al. |
| 2004/0116861 A1* | 6/2004 | Trocki .............. A61M 5/14546 604/131 |
| 2004/0133153 A1 | 7/2004 | Trocki et al. |
| 2004/0133183 A1 | 7/2004 | Trocki et al. |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0240149 A1 | 10/2005 | Lu |
| 2006/0129104 A1 | 6/2006 | Cowan et al. |
| 2006/0173411 A1 | 8/2006 | Barere |
| 2007/0123830 A1 | 5/2007 | Johannes, Sr. et al. |
| 2007/0191785 A1 | 8/2007 | Barere et al. |
| 2009/0247957 A1 | 10/2009 | Heutschi |
| 2010/0016796 A1 | 1/2010 | Derichs |
| 2010/0280369 A1 | 9/2010 | Bruce |
| 2010/0280370 A1 | 11/2010 | Namey, Jr. |
| 2010/0318030 A1 | 12/2010 | Jenkins |
| 2011/0178500 A1 | 7/2011 | Shang et al. |
| 2011/0224611 A1 | 9/2011 | Lum et al. |
| 2012/0039809 A1 | 2/2012 | Levinson et al. |
| 2012/0172817 A1* | 7/2012 | Bruggemann .... A61M 5/14566 604/218 |
| 2012/0184920 A1 | 7/2012 | Okihara et al. |
| 2012/0286187 A1 | 11/2012 | Spolski |
| 2013/0150806 A1 | 6/2013 | Fangrow, Jr. |
| 2013/0211325 A1 | 8/2013 | Wang et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0031763 A1 | 1/2014 | Soma et al. |
| 2014/0200483 A1 | 7/2014 | Fojtik |
| 2014/0243746 A1 | 8/2014 | Trocki et al. |
| 2014/0330216 A1 | 11/2014 | Weaver et al. |
| 2015/0025375 A1* | 1/2015 | Pollard ............. A61M 5/14546 600/432 |

FOREIGN PATENT DOCUMENTS

| | | |
|---|---|---|
| DE | 3227417 A1 | 2/1983 |
| DE | 4017920 A1 | 12/1991 |
| DE | 19601214 A1 | 8/1996 |
| DE | 19633530 A1 | 2/1998 |
| EP | 0111724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 0951306 B1 | 10/1999 |
| EP | 1002551 A2 | 5/2000 |
| EP | 1166807 A1 | 1/2002 |
| EP | 1166807 B1 | 11/2005 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |

(56) References Cited

FOREIGN PATENT DOCUMENTS

| | | | |
|---|---|---|---|
| WO | 8002376 | A1 | 11/1980 |
| WO | 8500292 | A1 | 1/1985 |
| WO | 8502256 | A1 | 5/1985 |
| WO | 8906145 | A1 | 7/1989 |
| WO | 8909071 | A1 | 10/1989 |
| WO | 8911310 | A1 | 11/1989 |
| WO | 9001962 | A1 | 3/1990 |
| WO | 9104759 | A1 | 4/1991 |
| WO | 9221391 | A1 | 12/1992 |
| WO | 9413336 | A1 | 6/1994 |
| WO | 9425089 | A1 | 11/1994 |
| WO | 9632975 | A1 | 10/1996 |
| WO | 9707841 | A2 | 3/1997 |
| WO | 9736635 | A1 | 10/1997 |
| WO | 9820920 | A2 | 5/1998 |
| WO | 9965548 | A1 | 12/1999 |
| WO | 0137903 | A2 | 5/2001 |
| WO | 0137905 | A2 | 5/2001 |
| WO | 0204049 | A1 | 1/2002 |
| WO | 03101527 | A1 | 12/2003 |
| WO | 2004035289 | A1 | 4/2004 |
| WO | 2005053771 | A2 | 6/2005 |
| WO | 2007130061 | A1 | 11/2007 |
| WO | 2010139793 | A1 | 12/2010 |
| WO | 2011129175 | A1 | 10/2011 |
| WO | 2012124028 | A1 | 9/2012 |
| WO | 2012155035 | A1 | 11/2012 |
| WO | 2015006430 | A1 | 1/2015 |
| WO | 2016069711 | A1 | 5/2016 |
| WO | 2016069714 | A1 | 5/2016 |

OTHER PUBLICATIONS

"International Search Report and Written Opinion from corresponding PCT Application No. PCT/US2015/021171", dated Jun. 23, 2015.
"Supplementary European Search Report in EP App. EP15765821", dated Oct. 24, 2017.
Brochure for "Angiomat 6000" of Liebel-Farsheim, 2111 E. Galbraith Road, Cincinnati, OH 45215, © 1987.
Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).
Brochure for "PercuPump 1A" of E-Z-Em, Inc, 717 Main Street, Westbury, NY 11590, © 1990.
Brochure for the "The First and Only True Injection System, " Medrad Mark V System, Control No. 85106-00-BA-02, Nov. 1988.
The International Search Report from corresponding PCT Application PCT/US2013/061384 dated Feb. 20, 2014.
"Extended European Search Report and Opinion from EP15823049", dated Feb. 1, 2017.
Feb. 23, 2015 ISR and WO from PCT/US2014/067435.
Injektron 82 MRT User Instructions, Version MR2, CEO535, Med-Tron GmbH(Mar. 10, 1999).
International Preliminary Report of Patentability dated Jan. 12, 2016 from PCT/US2014/045923.
International Search Report & Written Opinion for International Application No. PCT/US2004/039225, ISA/US, dated May 12, 2006.
"International Search Report and Written Opinion from PCT Application No. PCT/US2016/059245", dated Mar. 10, 2017.
"International Search Report and Written Opinion from PCT Application No. PCT/US2016/059246", dated Dec. 1, 2016.
International Search Report for Counterpart PCT Application No. PCT/US00/32271 dated Jul. 3, 2001.
International Search Report for International Application No. PCT/AU01/00830, dated Nov. 1, 2001.
International Search Report for International Application No. PCT/US03/17305, dated Oct. 21, 2003.
IPRP dated Jan. 12, 2016 from PCT/US2014/045923.
ISR dated Oct. 30, 2014 from PCT/US2014/045923.
ISR dated May 12, 2006 by PCT/US2004/039225.
ISR from PCT/US97/20122, dated Jun. 30, 1998.
Liebel-Flarsheim company—Angiomat 6000 Digital Injection System Operator's Manual, 600950 Rev 1 (1990); p. 3-6 to 3-8, 4-52 to 4-56.
Medrad Envision CT Injector Operation Manual, EOM 700E, 92401-T-123 Rev E, Copyright 1995.
Medrad Envision CT Injector Operation Manual, EOM 700E, 92401-T-123 Rev E, pp. 2-10 to 2-11 and pp. 2-30 to 2-35(Copyright 1995).
Medrad, Mark V/Mark V Plus Injector Operation Manual,KMP 805P Rev. B (1990); pp. 1-18 to 1-28, 3-7 to 3-13, 14-1 to 14-4.
Supplementary ESR from EP 01949108 dated Apr. 13, 2007.
Supplementary ESR from EP 01949108 dated Apr. 25, 2007.
Supplementary European Search Report dated Apr. 14, 2016 from EP13842045.
Supplementary Partial European Search Report for EP 01949108 dated Apr. 13, 2007.
The European Search Report dated Apr. 27, 2015 from corresponding EP Application No. EP14174725.
The International Preliminary Report on Patentability dated Apr. 9, 2015 from corresponding PCT Application No. PCT/US2013/061384.

* cited by examiner

SYSTEM FOR SYRINGE ENGAGEMENT TO AN INJECTOR

CROSS-REFERENCE TO RELATED APPLICATIONS

This application claims priority to U.S. Provisional Application No. 61/955,527, filed Mar. 19, 2014 and U.S. Provisional Application No. 61/970,018, filed on Mar. 25, 2014, the disclosures of which are incorporated herein by reference in their entirety.

BACKGROUND

Field

This application relates to medical injectors and syringes, syringe interfaces, and syringe plungers for use therewith. More particularly, the present application relates to front-loading medical injectors and syringes, syringe interfaces, and syringe plungers for use with new or existing medical injectors such that the syringe is mountable upon and removable from the injectors by a syringe latch.

Description of Related Art

Medical injectors and syringes for injecting contrast media into a patient for imaging biological structures are known in the art. For example, with reference to FIG. 1, a conventional injector apparatus 10 for injecting a liquid contrast media into a vascular system of an animal is disclosed in U.S. Pat. No. 5,383,858, which is incorporated herein by reference. This injector apparatus 10 has a front-loading construction. The apparatus of FIG. 1 utilizes a syringe 12 capable of being front-loaded into a mounting assembly 14 associated with a front wall 16 of a housing 18 of an injector 20 by a first releasable mechanism 22. The syringe 12 is capable of functioning in an injection operation without the use of a pressure jacket (although the syringe may be used in an injector with a pressure jacket).

With continued reference to FIG. 1, the mounting assembly 14 is provided with an essentially cylindrical interface 26 for receiving a rearward end of the syringe 12. The interface 26 includes an annular surface 28, which may be cylindrical or conically tapered. The annular surface 28 includes a distal ledge, which is engaged by tabs 30 on the rearward end of the syringe 12. The syringe 12 is inserted into the cylindrical interface 26 until the tabs 30 engage the distal ledge to secure the syringe 12 to the injector 20.

The syringe 12 comprises an elongated main tubular body or barrel 32 and a coaxial discharge injection section 34, interconnected by an intermediate conical portion 36. A plunger 38 is slidably positioned within the tubular body 32 and is connectable to a second releasable mechanism 40 on a piston 42 in the injector housing 18. The second releasable mechanism 40 is formed in part by the plunger 38 and in part by the piston 42.

The piston 42 and plunger 38 cooperate to eject fluid contained within the syringe 12 in a desired quantity and at a desired rate. The second releasable mechanism 40 is designed to facilitate axial movement of the plunger 38 in either direction when actuated. The second releasable mechanism 40 is also designed to engage or disengage the plunger 38 from the piston 42 no matter where the plunger 38 sits in tubular body 32.

In operation, the syringe 12 is mounted by inserting the syringe 12 into the interface 26 in the mounting assembly 14. The tabs 30 initially move past the annular surface 28 where they engage the distal ledge to securely hold the syringe 12 to the mounting assembly 14. The mounting assembly 14 further includes a forwardly projecting annular ring or collar 44, which functions to assure perpendicular engagement between the plunger 38 and piston 42. As explained above, the forwardly projecting annular ring or collar 44 also functions as a seal between a resilient annular sealing flange 46 on the syringe 12 and the mounting assembly 14.

The resilient annular sealing flange 46 surrounds the tubular body 32 of the syringe 12 and is disposed forward of the tabs 30 a preselected distance essentially equal to a width of the annular surface 28. Thus, when the syringe 12 is inserted into the interface 26 in the mounting assembly 14 until the sealing flange 46 engages the annular ring 44, the annular ring 44 and flange 46 create a seal between the syringe 12 and the mounting assembly 14.

With further reference to FIG. 1, the apparatus also includes a system for transmitting syringe information from the syringe 12 to an injector controller 51. The syringe 12 is provided with an encoding device 48 forward of the tabs 30 but rearward of the flange 46. When attaching the syringe 12 to the mounting assembly 14, if the syringe 12 is rotated after the tabs 30 engage the distal ledge, a sensor 50 is provided in the annular surface 28 to read the encoding device 48. The sensor 50 then forwards the associated signals to the injector controller 51, which interprets the signals and modifies the function of the injector 20 accordingly. Examples of the information which could be encoded on the encoding device 48 include dimensions of the syringe 12, volume of the syringe 12, content of the syringe 12 (in the case of a pre-filled syringe), manufacturing information such as lot numbers, dates and tool cavity number, recommended contrast media flow rates and pressures, and loading/injection sequences.

As an alternative to the encoding device 48 being a bar code, the encoding device 48 also could include machine-readable raised or recessed surfaces. In addition, the tubular body 32 of the syringe 12 also may be provided with an indicating mechanism 52 for readily detecting the presence or absence of a liquid contrast media in the syringe 12. In this instance, the indicating mechanism 52 includes a plurality of integrally molded, textured dots on the syringe 12, which provide a visual indication of whether the syringe 12 contains liquid or air.

Accordingly, while the above injector and syringe apparatus have proven effective, the engagement reliability of the mounting assembly 14 discussed hereinabove was found to be insufficient. Accordingly, a need has arisen for a more reliable syringe/injector engagement interface.

SUMMARY

According to one aspect of the device of the present disclosure, provided is an injector system for injecting fluid that includes a syringe and an injector. The syringe includes: a body comprising a rearward end and a forward end; a plunger movably disposed within the body; at least one syringe drive paw positioned toward the rearward end of the body; and a syringe engagement flange positioned toward the rearward end of the body and extending around a circumference of the body. The injector includes: a housing having a front plate defining a syringe-receiving opening therein and a drive member at least partially disposed within the housing and operable to engage the plunger disposed within the syringe. The syringe latch has a plurality of latch members extending toward a center of the syringe-receiving opening and configured to move from a closed position to an open position when a force is applied thereto and from the open position to the closed position when the force is removed therefrom. The syringe engagement flange pushes against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing.

The injector may further include a syringe release gear that forms an enclosure for receiving the syringe when the syringe is fully seated within the housing. The syringe release gear may be mounted to a rear side of the front plate by at least one syringe release cam pin. The syringe release gear may also include an opening formed therein that is aligned with the syringe-receiving opening of the front plate. The opening in the syringe release gear may include a plurality of teeth formed around a circumference thereof. In addition, the syringe drive paw may be configured to engage the plurality of teeth of the opening of the syringe release gear.

The syringe may be disengaged from the injector after completion of an injection procedure by rotating the syringe. This causes rotation of the syringe release gear via the engagement between the syringe drive paw and the plurality of teeth of the syringe release gear. The plurality of latch members of the syringe latch are thereby forced into the open position which allows a user to remove the syringe from the housing of the injector. The syringe desirably includes two syringe drive paws that are positioned toward the rearward end of the body located 180° degrees apart.

The syringe latch may include two latch members, three latch members, or any other suitable number of latch members. Each of the plurality of latch members of the syringe latch may include a first portion and an arc-shaped second portion extending from the first portion. The arc-shaped second portion, when viewed in cross-section, may include a sloping face. The syringe latch may be manufactured from a polymeric material.

According to another aspect of the present disclosure, also provided is a method for engaging a syringe with an injector. The method includes: providing a syringe having a body with a rearward end and a forward end, a plunger movably disposed within the body, a syringe drive paw positioned toward the rearward end of the body, and a syringe engagement flange positioned toward the rearward end of the body and extending around a circumference of the body; providing an injector that includes a housing having a front plate defining a syringe-receiving opening therein, a drive member at least partially disposed within the housing and operable to engage the plunger disposed within the syringe; and a syringe latch mounted to a front side of the front plate and comprising a plurality of latch members extending toward a center of the syringe-receiving opening and configured to move from a closed position to an open position when a force is applied thereto and from the open position to the closed position when the force is removed therefrom; applying axial rearward motion to the syringe relative to the syringe latch such that the syringe engagement flange pushes against the plurality of latch members of the syringe latch to open the syringe latch; and returning the plurality of latch members of the syringe latch to the closed position to retain the syringe within the opening of the housing when the syringe is fully seated within the housing.

According to another aspect of the present disclosure, an injector system for injecting fluid may include a syringe having a body comprising a rearward end and a forward end, and a plunger movably disposed within the body, the plunger having at least one flexible leg extending toward the rearward end of the body. The injector system may further include an injector having a housing having a front plate defining a syringe-receiving opening therein, a drive member at least partially disposed within the housing and operable to engage the plunger disposed within the syringe and releasably connect the at least one flexible leg to at least a portion of the drive member, a syringe release gear that forms an enclosure for receiving the syringe when the syringe is fully seated within the housing, the syringe release gear mounted to a rear side of the front plate, and a plunger release tube surrounding at least a portion of the drive member, the plunger release tube having a first end rotationally engaged with the syringe release gear. Rotation of the syringe release gear may rotate and axially move the plunger release tube relative to the drive member to engage the at least one flexible leg and release the at least one flexible leg from the drive member.

According to a further aspect of the present disclosure, the syringe release gear may be mounted to a rear side of the front plate by at least one syringe release cam pin. The syringe release cam pin may extend through the front plate. The syringe release gear may include an opening formed therein that is aligned with the syringe-receiving opening of the front plate. The opening in the syringe release gear may include a plurality of teeth formed around a circumference thereof. At least one syringe drive paw may be positioned toward the rearward end of the body and a syringe engagement flange may be positioned toward the rearward end of the body and extending around a circumference of the body. The injector may further include a syringe latch mounted to a front side of the front plate, the syringe latch comprising a plurality of latch members extending toward a center of the syringe-receiving opening and configured to move from a closed position to an open position when a force is applied thereto and from the open position to the closed position when the force is removed therefrom, The syringe engagement flange may push against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing. The syringe drive paw may be configured to engage a plurality of teeth formed on the syringe release gear. The syringe may be disengaged from the injector after completion of an injection procedure by rotating the syringe, which causes rotation of the syringe release gear via the engagement between the syringe drive paw and a plurality of teeth of the syringe release gear, thereby forcing the plurality of latch members into the open position and allowing a user to remove the syringe from the housing of the injector. Each of the plurality of latch members of the syringe latch may include a first portion and an arc-shaped second portion extending from first portion. The arc-shaped portion may include a slot formed therein. The syringe may include two syringe drive paws positioned toward the rearward end of the body and located 180° degrees apart.

According to another aspect of the present disclosure, a front-loading medical injector system may include a syringe having a body comprising a rearward end and a frontward end, and a plunger movably disposed within the body, the plunger having at least one flexible leg extending toward the rearward end of the body. The injector system may further include an injector having a housing having a front plate defining a syringe-receiving opening therein, a drive member at least partially disposed within the housing and operable to engage the plunger disposed within the syringe and releasably connect the at least one flexible leg to at least a portion of the drive member, and a syringe release assembly operable to release the syringe. Rotation of the syringe release assembly may release the at least one flexible leg from the drive member. The syringe release assembly may include a syringe release gear that forms an enclosure for receiving the syringe when the syringe is fully seated within the housing, the syringe release gear mounted to a rear side of the front plate, and a plunger release tube surrounding at least a portion of the drive member, the plunger release tube having a first end rotationally engaged with the syringe release gear. Rotation of the syringe release gear may rotate and axially move the plunger release tube relative to the drive member to engage the at least one flexible leg and release the at least one flexible leg from the drive member. The injector may further include a syringe latch mounted to a front side of the front plate for securing the syringe to the injector. The syringe latch may have a plurality of latch members extending toward a center of the syringe-receiving opening and configured to move from a closed position to an open position when a force is applied thereto and from the open position to the closed position when the force is removed therefrom. At least one syringe drive paw may be positioned toward the rearward end of the body, and a syringe engagement flange may positioned toward the rearward end of the body and extending around a circumference of the body. The syringe engagement flange may push against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing. Each of the plurality of latch members of the syringe latch may include a first portion and an arc-shaped second portion extending from first portion.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

DETAILED DESCRIPTION

Figure 1:
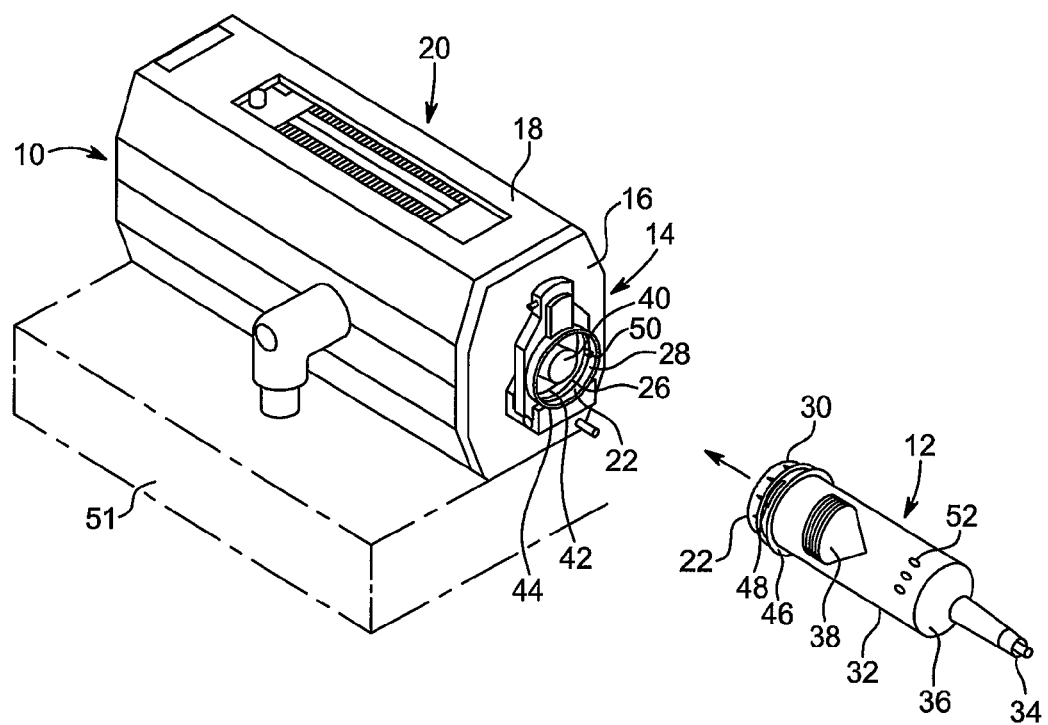
FIG. 1 is a perspective view of a conventional injector system showing an injector housing and a syringe in a disassembled relationship.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

Figure 2:
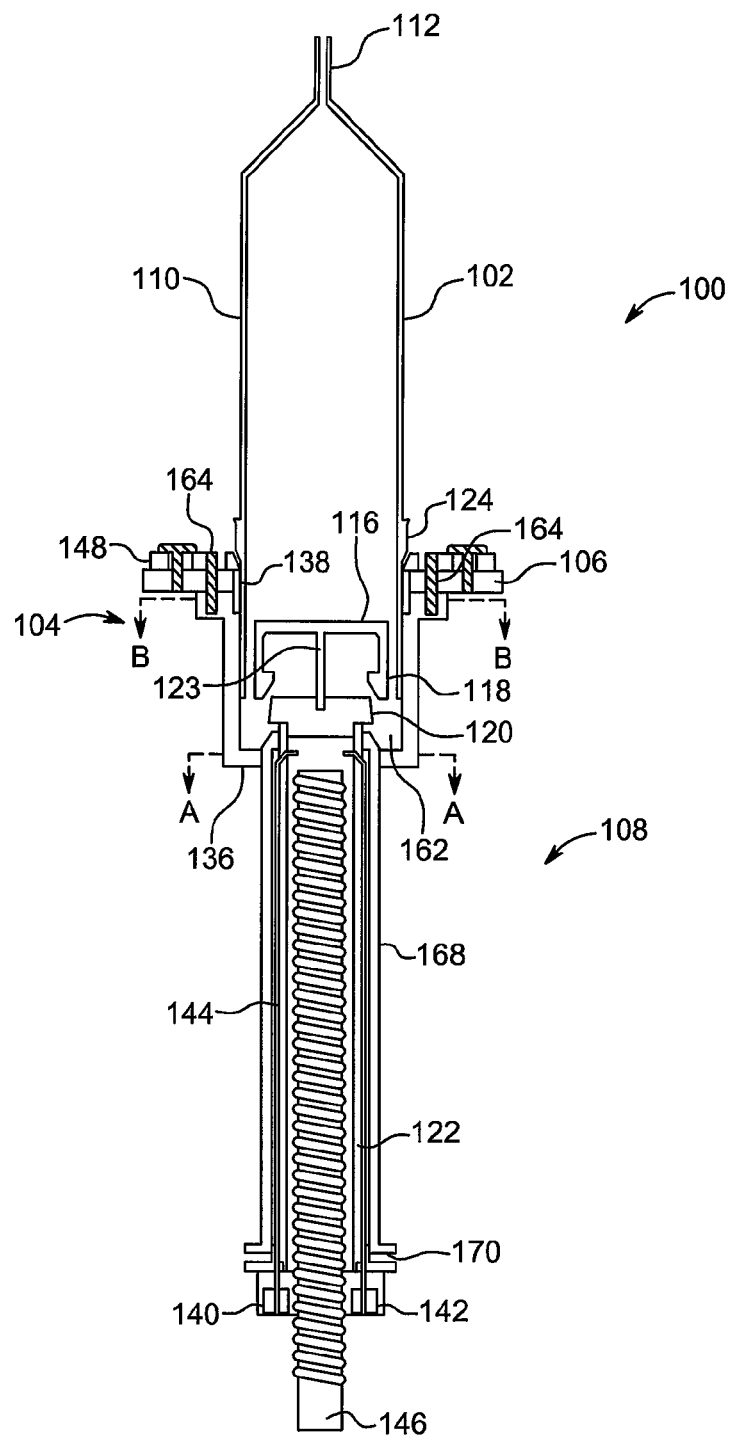
FIG. 2 is a cross-sectional view of an injector system in accordance with an embodiment of the disclosure showing the syringe and the injector housing in a partially disassembled relationship.

With reference to FIG. 2, an injector system 100 for injecting a liquid contrast media into a vascular system of an animal is provided. The injector system 100 has a front-loading construction. The system of FIG. 2 utilizes a syringe 102 capable of being front-loaded into a mounting assembly 104 associated with a front plate 106 of a housing (not shown) of an injector 108 by a first releasable mechanism 22. The syringe 102 is capable of functioning in an injection operation without the use of a pressure jacket (although the syringe may be used in an injector with a pressure jacket).

The syringe 102 includes an elongated main tubular body or barrel 110 and a coaxial discharge injection section 112 interconnected by an intermediate conical portion 114. A plunger 116 is slidably positioned within the tubular body 110 and includes at least one plunger connect flex leg 118 that is connectable to a piston/plunger interface 120 on a piston 122 of the injector 108. The plunger 116 also includes a plunger sense interrupter 123 extending from a central portion thereof in the direction of the at least one flex leg 118. The plunger sense interrupter 123 is configured to interrupt a light path produced by an IR transmitter 140 and IR receiver 142 through a fiber optic cable 144 extending along the length of the piston 122, thereby providing a signal to an injector controller (not shown) that the syringe 102 is fully seated within the injector 108. An alternative embodiment of the plunger sense interrupter 123 determines the presence/absence of the syringe 102 without the use of a fiber optic cable.

The syringe 102 further includes a syringe engagement flange 124 positioned toward the rearward end of the body 110 and extending around a circumference of the body 110. When viewed in cross-section, the syringe engagement flange 124 includes a sloping section 126, a shoulder section 128 extending from the sloping section 126 that is essentially perpendicular to an exterior surface of the body 110 of the syringe 102, and an engagement section 130 extending from the shoulder section 128. The engagement section 130 is configured to engage a plurality of teeth 132 of an opening 134 of a syringe release gear 136 of the injector 108 as discussed in greater detail hereinafter in relation to FIG. 6.

Since the syringe 102 is being used in this embodiment without a pressure jacket, for strength and visibility of the contents of the syringe 102, the syringe 102 may be formed of a clear PET polyester material. In the alternative, the wall of the syringe 102 may be formed of polypropylene reinforced by providing a series of annular ribs on the tubular body 110 of the syringe 102 in a longitudinally spaced relationship. In addition, the syringe 102 desirably includes an encoding device for providing information regarding the syringe 102 to the injector 108 an indicating mechanism for readily detecting the presence or absence of a liquid contrast media in the syringe 102 similar to the encoding device and indicating mechanism of syringe 12 discussed hereinabove.

With continued reference to FIG. 1, the injector includes a housing (not shown) having the front plate 106 defining a syringe-receiving opening 138 therein. The piston 122 is positioned within the housing and is configured to extending into and out of the syringe-receiving opening 138 under the power of a drive mechanism 146. The piston 122 includes the piston/plunger interface 120 at an end thereof that is operable to interact with the at least one flex leg 118 of the plunger 116 to engage the plunger 116 disposed within the syringe 102.

Figure 3:
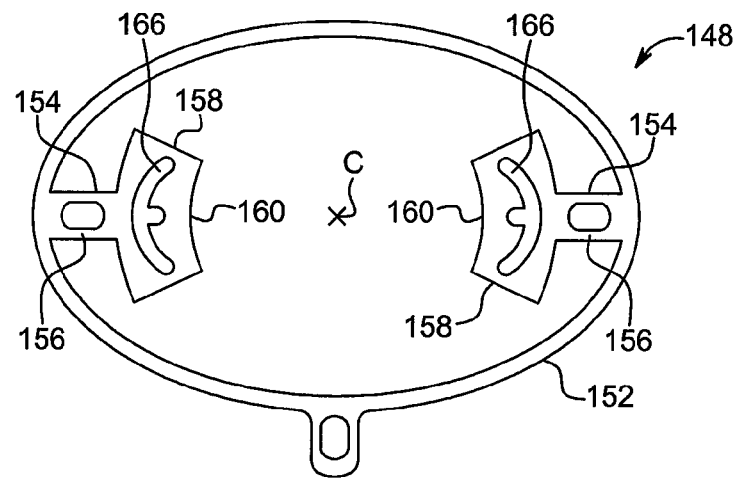
FIG. 3 is a top plan view of the syringe latch in accordance with an embodiment of the disclosure for connecting the syringe to the injector housing.

With reference to FIG. 3 and with continuing reference to FIG. 2, the injector 108 also includes a syringe latch 148 mounted to a front side of the front plate 106 by any suitable fastening device 150 for maintaining the syringe in the seated position within the injector 108. The syringe latch 148 comprises a substantially oval shaped body member 152 and a plurality of latch members 154 extending toward a center C of the body member 152. In the embodiment of the syringe latch 148 illustrated in FIG. 3, two latch members 154 are included. The syringe latch 148 is desirably manufactured from a resilient, polymeric material such that the latch members 154 are configured to move from a closed position to an open position when a force is applied thereto and from the open position to the closed position when the force is removed therefrom.

Each of the plurality of latch members 154 of the syringe latch 148 includes a first portion 156 extending from the body member 152 and an arc-shaped second portion 158 extending from the first portion 156 and configured to engage the syringe engagement flange 124 of the syringe 102. The arc-shaped second portion 158, when viewed in cross-section, may include a sloping face 160 (see FIGS. 4A-4E) that engages with the sloping section 126 of the syringe engagement flange 124 to force the syringe latch 148 into the open position.

With continued reference to FIG. 2, the injector 108 also includes the syringe release gear 136 that forms an enclosure 162 for receiving the syringe 102 when the syringe 102 is fully seated within the injector housing. The syringe release gear 136 is mounted to a rear side of the front plate 106 by at least one syringe release cam pin 164. The syringe release cam pin 164 is configured to be connected to the syringe release gear 136 and extend through the front plate 106 of the injector 108 into a slot 166 in the arc-shaped second portion 158 of the latch members 154 of the syringe latch 148.

Figure 7:
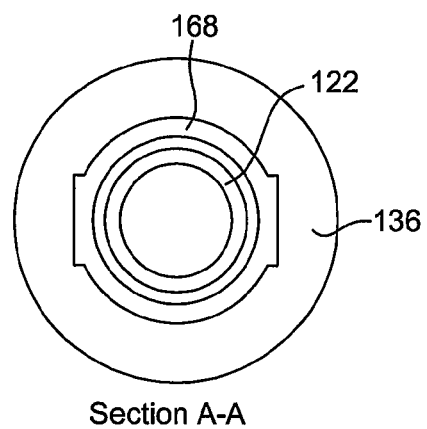
FIG. 7 is a cross-sectional view of the injector system of FIG. 2 taken along line A-A.

With reference to FIG. 7 and with continued reference to FIG. 2, the piston 122 is surrounded by a plunger release tube 168. The plunger release tube 168 has a first end that is rotationally engaged with the syringe release gear 136 such that rotation of the syringe release gear 136 causes rotation of the plunger release tube 168.

The process for engaging a syringe 102 with the injector 108 to form an injector system 100 is illustrated in FIGS. 4A-4E. This process allows for syringe engagement with an injector 108 that provides a syringe engagement adapted to releasably engage the syringe 102 with the injector 108 regardless of the rotational orientation of the syringe 102 with respect to the injector 108. The syringe engagement uses the flex legs 118 attached to the back side of the plunger 116 of the syringe 102 and a corresponding feature on the piston 122 of an injector 108 that provides axial engagement that does not require any specific rotational orientation of the syringe 102 to releasably engage with the injector 108. Additionally, a feature (i.e., the syringe engagement flange 124) is provided on the outside surface of the rear portion of the tubular body 110 to transfer rotational movement of the syringe into a release mechanism (i.e., the syringe release gear 136) implemented in the injector 108 releasing both the syringe 102 and the plunger 116 regardless of the axial position of the engaged syringe plunger 116.

Figure 4A:
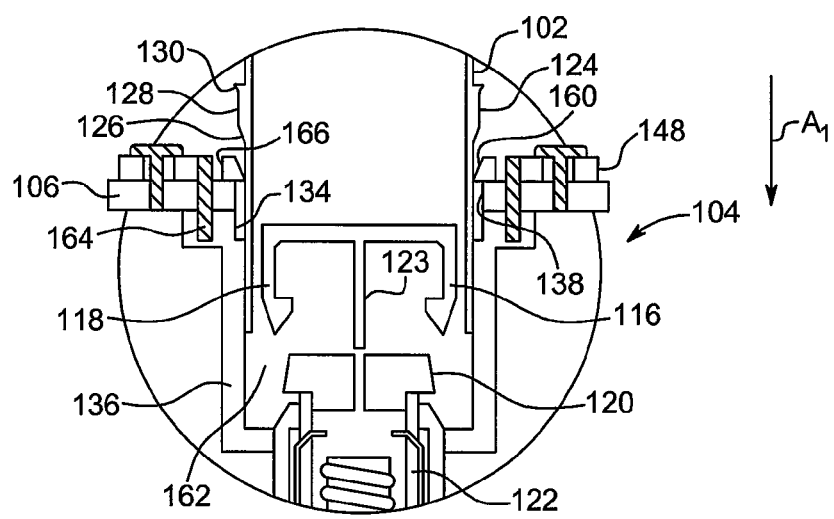
FIGS. 4A-4E are cross-sectional views of a portion of the injector system of FIG. 2 illustrating the steps required for loading a syringe into the injector housing.
Figure 4B:
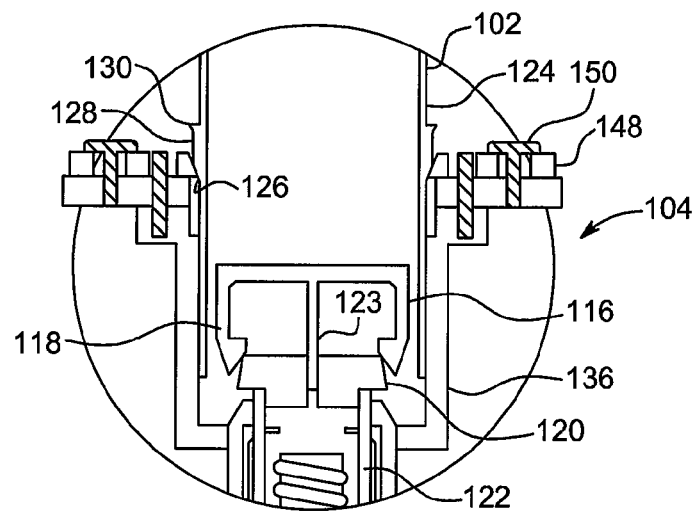
Figure 4C:
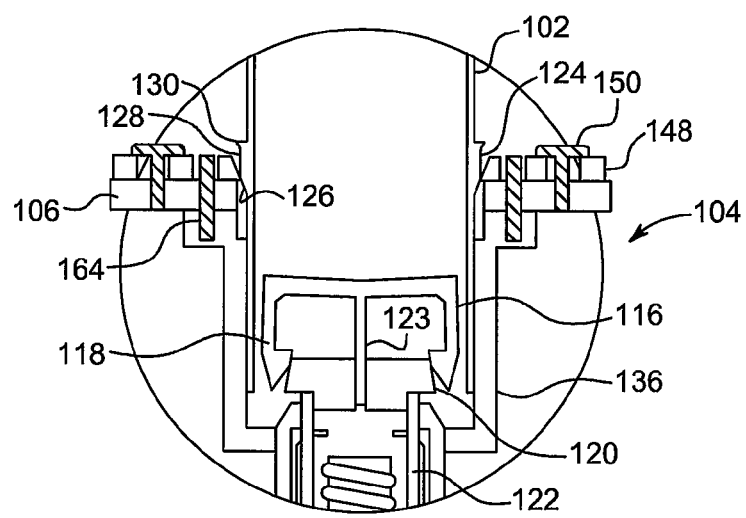
Figure 4D:
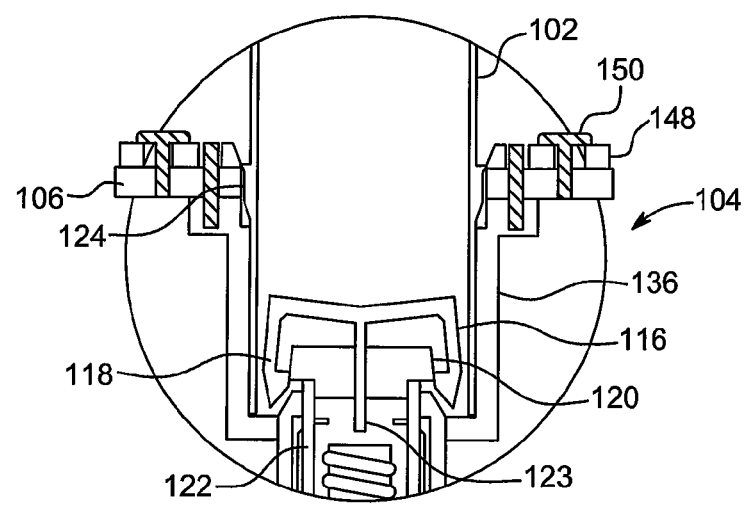
Figure 4E:
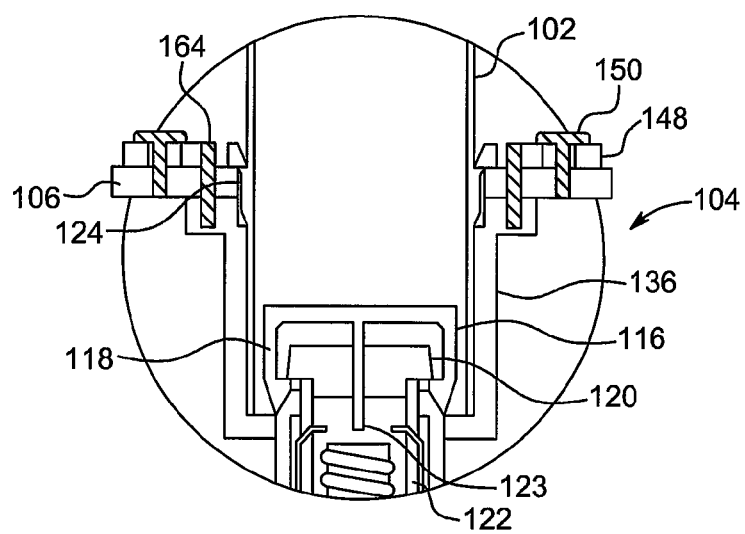

The first step in the process for engaging the syringe 102 with the injector 108 is shown in FIG. 4A in which the syringe 102 is positioned axially with the syringe-receiving opening 134 of the front plate 106 of the injector 108 and is moved axially along the piston 122 into the enclosure 162 formed by the syringe release gear 136 in the direction of arrow $A_1$. With reference to FIG. 4B, as the syringe 102 is inserted, the sloping section 126 of the syringe engagement flange 124 engages the sloping face 160 of the arc-shaped second section 158 of the latch members 154 of the syringe latch 148 and pushes the syringe latch 148. In addition, with reference to FIGS. 4C and 4D, as the syringe 102 is inserted, the sloped surface of the piston/plunger interface 120 flexes the at least one flex leg 118 of the plunger 116 open. With reference to FIG. 4E, continual movement of the syringe 102 in the direction of arrow $A_1$ causes the syringe 102 to be fully seated within the enclosure 162 formed by the syringe release gear 136. When the body of the syringe 102 is fully seated within the enclosure 162 formed by the syringe release gear 136, the following items occur: first, the engagement section 130 of the syringe engagement flange 124 engages the teeth 132 of the syringe release gear 136. In addition, the syringe engagement flange 124 moves beyond the arc-shaped second portion 158 of the latch members 154 of the syringe latch 148, thereby closing the syringe latch 148 to retain the syringe 102. Desirably, when the syringe latch 148 returns to the closed position, it provides an audible "click" to indicate to the operator that the syringe 102 has been installed on the injector 108. Furthermore, the flex legs 118 on the plunger 116 flex closed engaging the piston/plunger interface 120. Finally, the plunger sense interrupter 123 of the plunger 116 interrupts the light path produced by an IR transmitter 140 and IR receiver 142 through a fiber optic cable 144 extending along the length of the piston 122, thereby providing a signal to an injector controller (not shown) that the syringe 102 is fully seated within the injector 108.

Removal of the syringe 102 from the injector 108 upon the completion of an injection procedure requires that the syringe 102 be rotated, as described below. This operation is illustrated in and described by reference to FIGS. 8A-8D.

Figure 6:
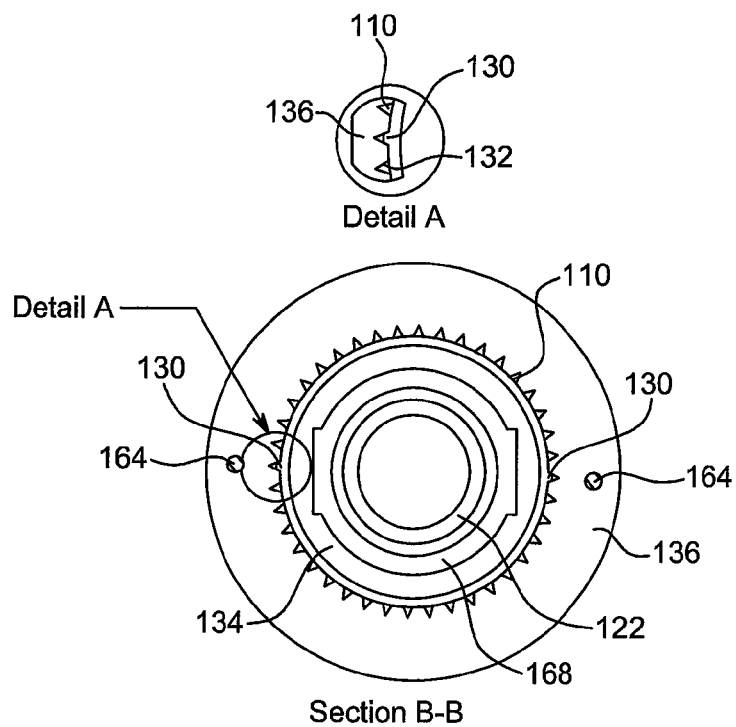
FIG. 6 is a cross-sectional view of the injector system of FIG. 2 taken along line B-B.
Figure 8A:
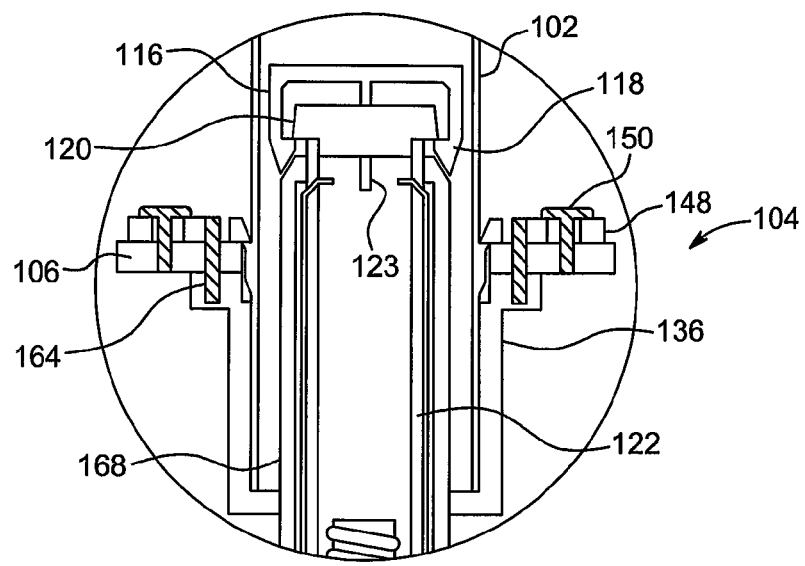
FIGS. 8A-8D are cross-sectional views of a portion of the injector system of FIG. 5 illustrating the steps required for unloading a syringe from the injector housing.
Figure 8B:
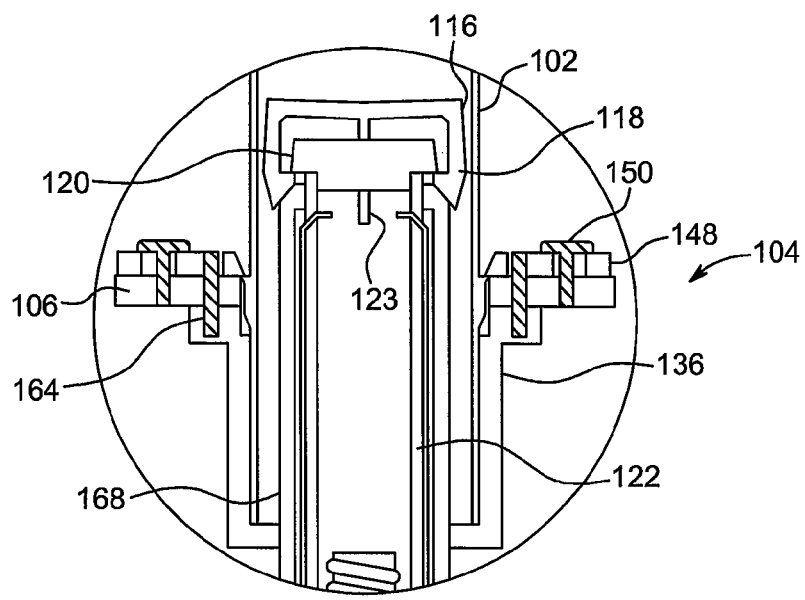
Figure 8C:
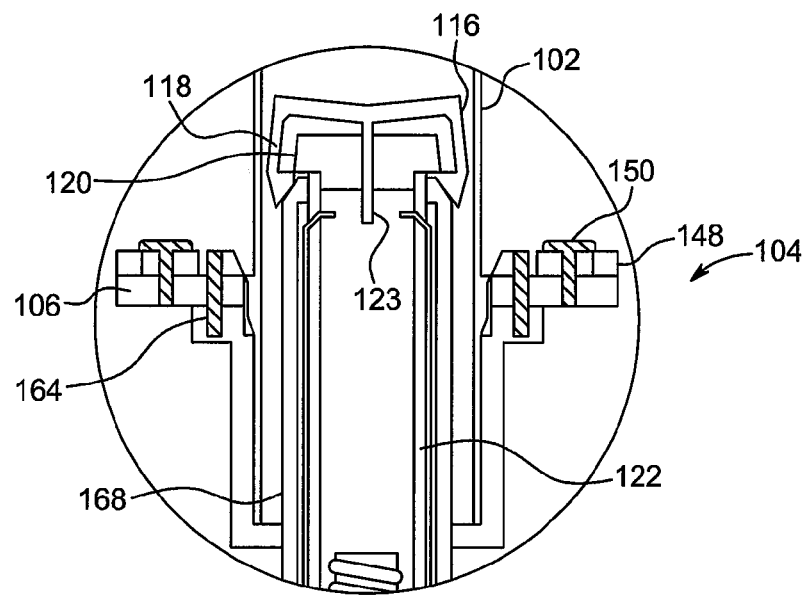

With reference to FIG. 8A and FIG. 8B, the rotation of the syringe 102 causes rotation of the syringe release gear 136 via the engagement between the engagement section 130 of the syringe engagement flange 124 and the plurality of teeth 132 of the syringe release gear 136 as shown in FIG. 6. This rotation, in turn, causes rotation of the syringe release cam pins 164 along the slots 166 provided in the latch members 154 of the syringe latch 148 as shown in FIG. 8C. The latch members 154 of the syringe latch 148 are thereby forced into the open position.

Figure 5:
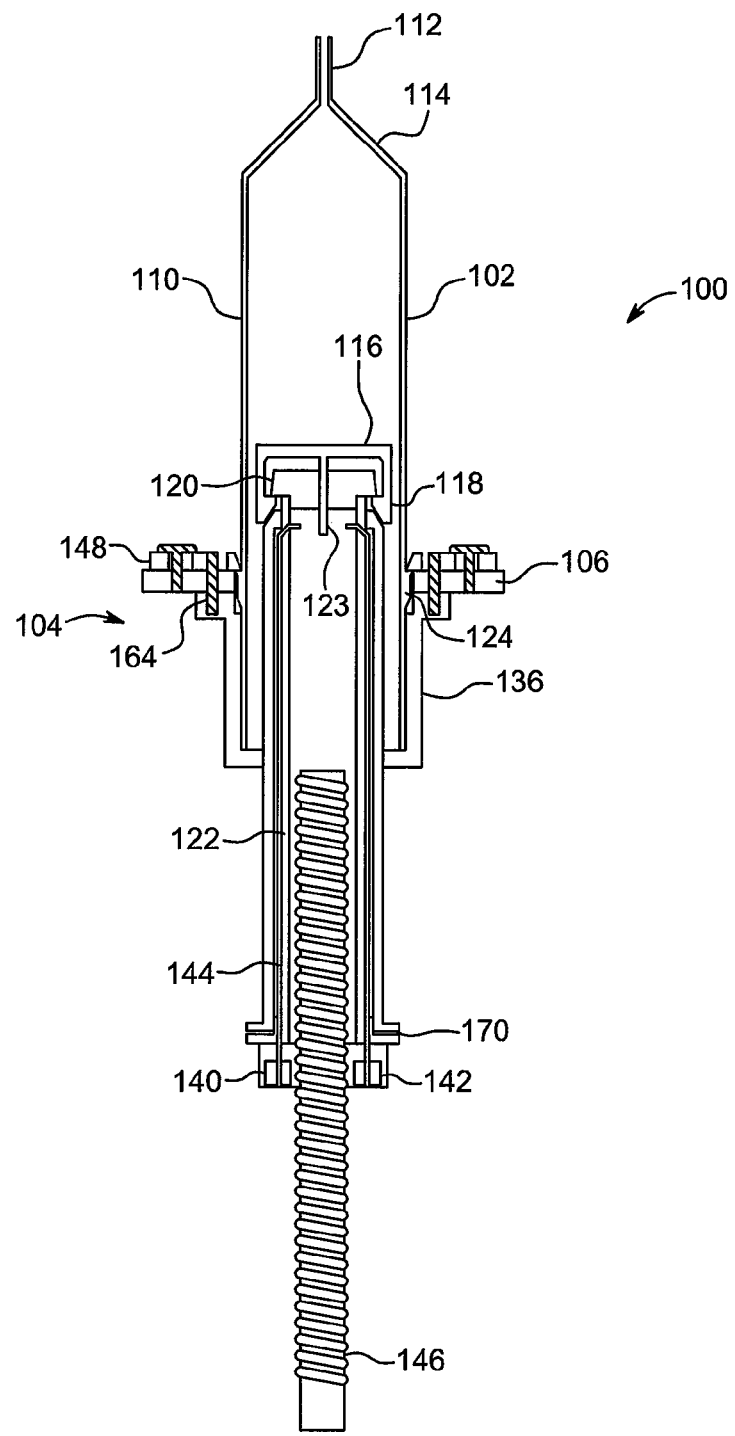
FIG. 5 is a cross-sectional view of the injector system of FIG. 2 showing the syringe and the injector housing in the assembled state.

As also shown in FIG. 8C, the rotation of the syringe release gear 136 also rotates the plunger release tube 168 about the piston 122 since the plunger release tube 168 is coupled to the syringe release gear 136 as described hereinabove. The rotation of the plunger release tube 168 about the piston 122 causes a cam action at a release cam surface 170 (see FIGS. 1 and 5) causing an axial extension of the plunger release tube 168 towards the syringe-receiving opening 134 of the front plate 106. The axial extension of the plunger release tube 168 forces the at least one flex leg 118 of the plunger 116 to flex open to release the piston/plunger interface 122.

Figure 8D:
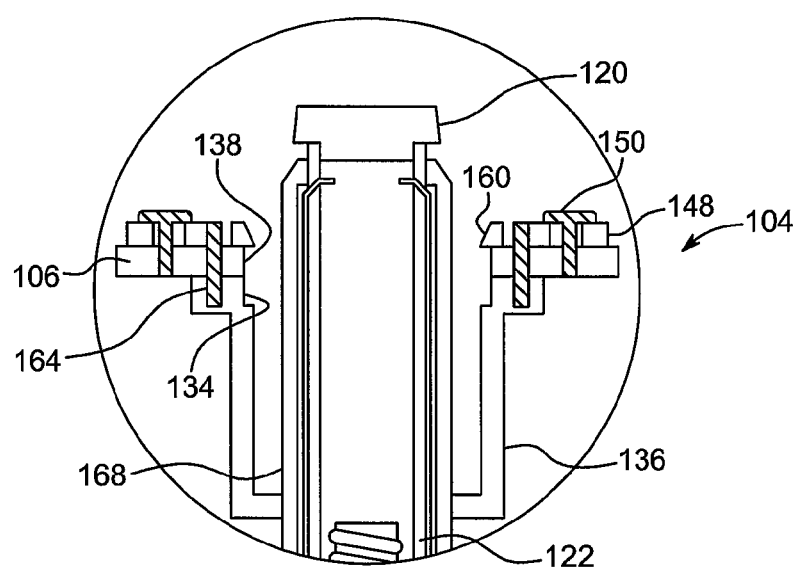
Figure 9:
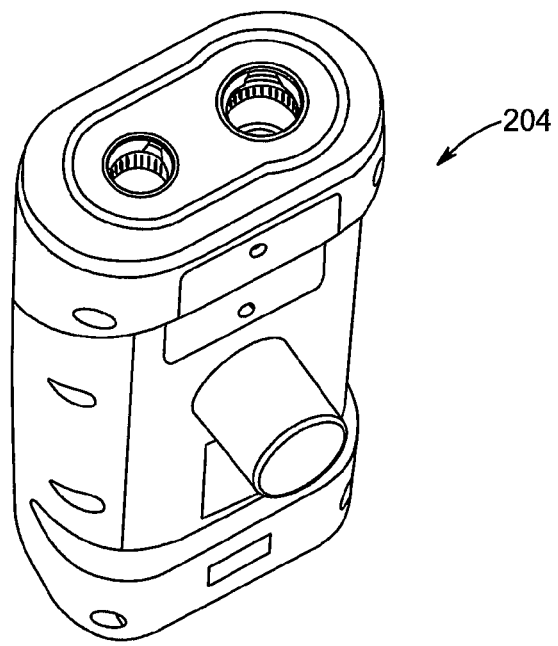
FIG. 9 is a perspective view of an injector in accordance with an alternative embodiment of the disclosure.

At this point, a user can remove the syringe 102 from the housing of the injector 108. Once the syringe 102 is removed, the syringe release gear 136 returns to original position allowing the syringe latch 148 to return to the closed position and the plunger release tube 168 to drop down as shown in FIG. 8D.

Figure 10:
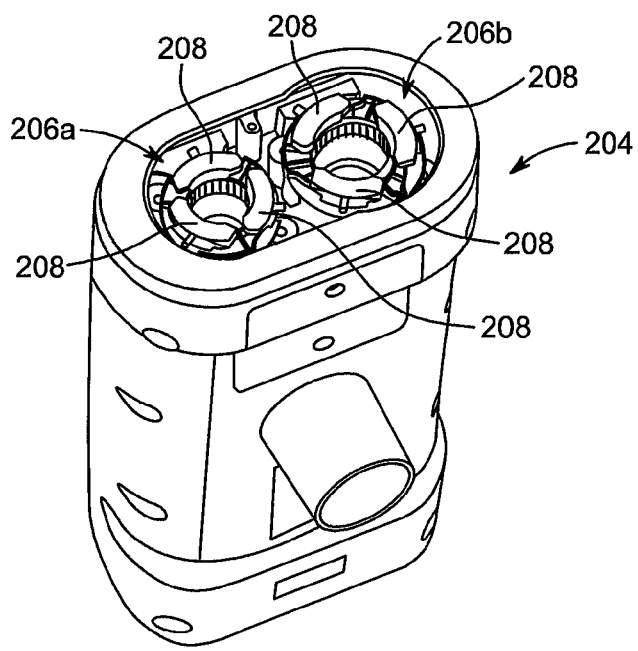
FIG. 10 is a perspective view of the injector of FIG. 9 having the faceplate removed such that an alternative embodiment of the syringe latch is visible.
Figure 11:
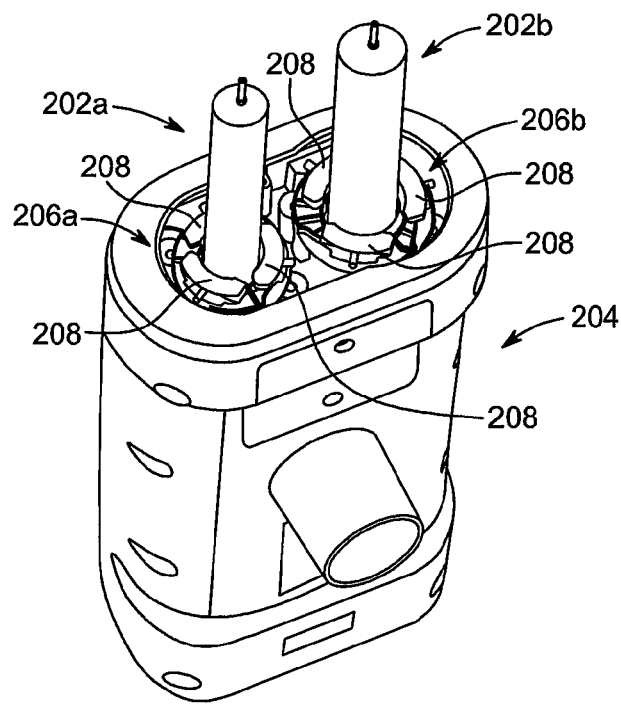
FIG. 11 is a perspective view of the injector of FIG. 10 with syringes attached thereto.
Figure 12:
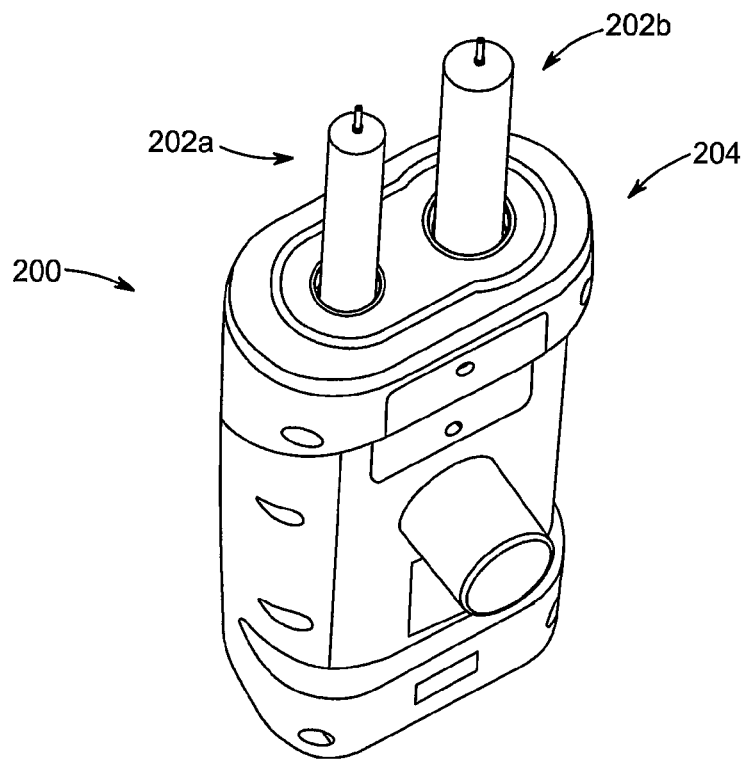
FIG. 12 is a perspective view of the injector of FIG. 9 with syringes attached thereto.

While the syringe latch 148 discussed hereinabove includes two latch members, this is not to be construed as limiting the disclosure as any suitable number of latch members may be utilized. For instance, with reference to FIGS. 9-14, the injector may be embodied as a dual syringe injector system 200 that includes a pair of syringes 202a, 202b and an injector 204. As shown in FIGS. 10 and 11, the injector 204 utilizes a syringe latch 206a, 206b for each of the syringes 202a, 202b that includes three latch members 208 for engaging the syringe 202a, 202b within the injector 204. In addition, rather than having the latch members 208 connected to a body member as with the syringe latch 148 discussed hereinabove, each of the latch members 208 is independent and utilizes a spring return 210 (see FIG. 14).

Figure 13:
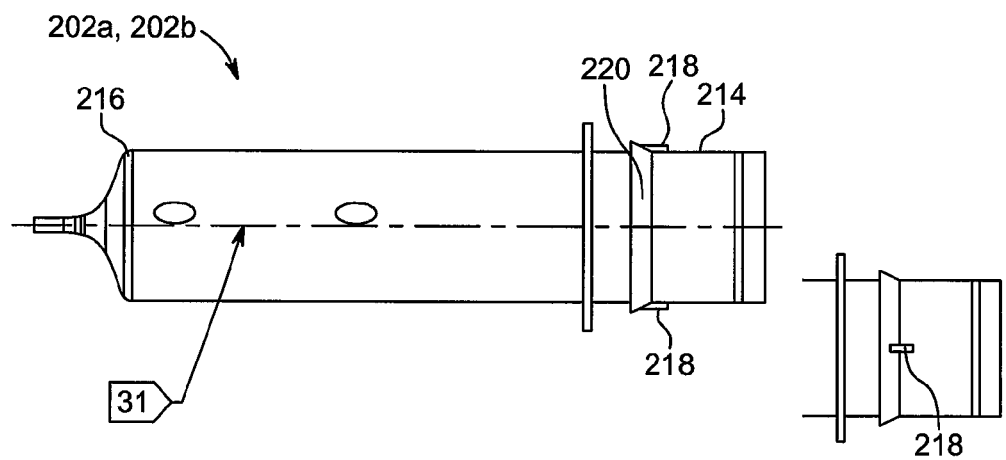
FIG. 13 is a side view of a syringe configured to be used with the injector of FIG. 9.
Figure 14:
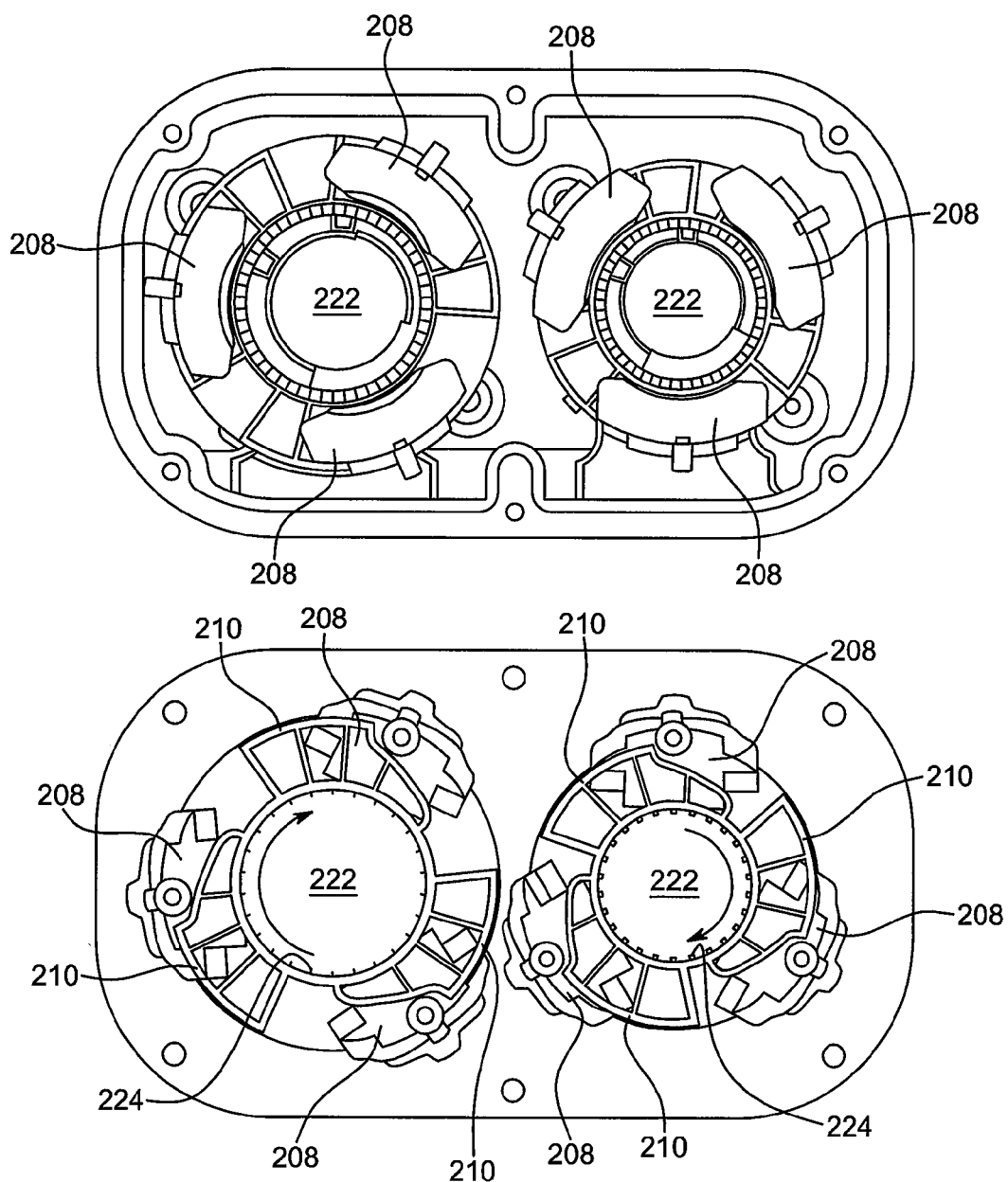
FIG. 14 is are front views of the syringe latch of the injector of FIG. 9.

More specifically, with reference to FIGS. 13 and 14, a syringe 202a, 202b for use with injector 204 includes a body 212 comprising a rearward end 214 and a forward end 216; a plunger (not shown) movably disposed within the body 212; and at least one syringe drive paw 218 positioned toward the rearward end 214 of the body 216. Desirably, the syringe 202a, 202b includes a pair of syringe drive paws 218 at the rearward end 214 of the body 216 located 180° apart. The syringe 202a, 202b also includes a syringe engagement flange 220 positioned toward the rearward end 214 of the body 212 and extending around a circumference of the body 212.

The injector 204 includes a pair of syringe latches 206a, 206b mounted to a front side of the front plate thereof. Each of the syringe latches 206a, 206b comprises a plurality of latch members 208 extending toward a center of the syringe-receiving opening 222 and configured to move from a closed position to an open position when a force is applied thereto and from the open position to the closed position when the force is removed therefrom. The syringe engagement flange 220 pushes against the plurality of latch members 208 of the syringe latch 206a, 206b to open the syringe latch 206a, 206b as axial rearward motion is applied to the syringe 202a, 202b relative to the syringe latch 206a, 206b and the plurality of latch members 208 return to the closed position to retain the syringe 202a, 202b within the opening 222 of the injector 204 when the syringe 202a, 202b is fully seated within the injector 204.

The syringe 202a, 202b may be disengaged from the injector 204 after completion of an injection procedure by rotating the syringe 202a, 202b. This causes rotation of a syringe release gear 224 via the engagement between the syringe drive paws 218 and a plurality of teeth of the syringe release gear 224. The rotation of the syringe release gear 224 activates the spring returns 210, which force the latch members 208 of the syringe latch 206a, 206b into the open position, thereby allowing a user to remove the syringe 202a, 202b from the injector 204.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

We claim:

1. An injector system for injecting a fluid comprising:
a syringe comprising:
  a body comprising a rearward end and a forward end;
  a plunger movably disposed within the body, the plunger having at least one flexible leg extending toward the rearward end of the body; and
an injector comprising:
  a housing having a front plate defining a syringe-receiving opening therein;
  a drive member at least partially disposed within the housing and operable to engage the plunger disposed within the syringe and releasably connect the at least one flexible leg to at least a portion of the drive member;
  a syringe release gear that forms an enclosure for receiving the syringe when the syringe is fully seated within the housing, the syringe release gear mounted to a rear side of the front plate; and
  a plunger release tube surrounding at least a portion of the drive member, the plunger release tube having a first end rotationally engaged with the syringe release gear and a second end opposite the first end, wherein rotation of the syringe release gear rotates the plunger release tube and rotation of the plunger release tube causes a cam action at a release cam surface provided at the second end of the plunger release tube causing an axial extension of the plunger release tube relative to the drive member such that the plunger release tube engages the at least one flexible leg and releases the at least one flexible leg from the drive member.

2. The injector system of claim 1, wherein the syringe release gear is mounted to the rear side of the front plate by at least one syringe release cam pin.

3. The injector system of claim 2, wherein the at least one syringe release cam pin extends through the front plate.

4. The injector system of claim 1, wherein the syringe release gear includes an opening formed therein that is aligned with the syringe-receiving opening of the front plate.

5. The injector system of claim 4, wherein the opening in the syringe release gear includes a plurality of teeth formed around a circumference thereof.

6. The injector system of claim 1, further comprising at least one syringe drive paw positioned toward the rearward end of the body; and
   a syringe engagement flange positioned toward the rearward end of the body and extending around a circumference of the body.

7. The injector system of claim 6, further comprising a syringe latch mounted to a front side of the front plate, the syringe latch comprising a plurality of latch members extending toward a center of the syringe-receiving opening and configured to move from a closed position to an open position when a force is applied thereto and from the open position to the closed position when the force is removed therefrom,
   wherein the syringe engagement flange pushes against the plurality of latch members of the syringe latch to open the syringe latch as axial rearward motion is applied to the syringe relative to the syringe latch and the plurality of latch members return to the closed position to retain the syringe within the opening of the housing when the syringe is fully seated within the housing.

8. The injector system of claim 7, wherein each of the plurality of latch members of the syringe latch includes a first portion and an arc-shaped second portion extending from the first portion.

9. The injector system of claim 8, wherein the arc-shaped portion includes a slot formed therein.

10. The injector system of claim 6, wherein the syringe drive paw is configured to engage a plurality of teeth formed on the syringe release gear.

11. The injector system of claim 6, wherein the syringe is disengaged from the injector after completion of an injection procedure by rotating the syringe, which causes rotation of the syringe release gear via an engagement between the at least one syringe drive paw and a plurality of teeth of the syringe release gear, thereby forcing a plurality of latch members into an open position and allowing a user to remove the syringe from the housing of the injector.

12. The injector system of claim 1, wherein the syringe includes two syringe drive paws positioned toward the rearward end of the body and located 180° degrees apart.

13. A method for engaging a syringe with an injector, comprising:
   providing the syringe comprising:
      a body comprising a rearward end and a forward end;
      a plunger movably disposed within the body, the plunger having at least one flexible leg extending toward the rearward end of the body; and
   providing the injector comprising:
      a housing having a front plate defining a syringe-receiving opening therein;
      a drive member at least partially disposed within the housing and operable to engage the plunger disposed within the syringe and releasably connect the at least one flexible leg to at least a portion of the drive member;
      a syringe release gear that forms an enclosure for receiving the syringe when the syringe is fully seated within the housing, the syringe release gear mounted to a rear side of the front plate; and
      a plunger release tube surrounding at least a portion of the drive member, the plunger release tube having a first end rotationally engaged with the syringe release gear and a second end opposite the first end;
   rotating the syringe release gear to rotate the plunger release tube;
   causing, by rotation of the plunger release tube, a cam action at a release cam surface provided at the second end of the plunger release tube causing an axial extension of the plunger release tube relative to the drive member such that the plunger release tube engages the at least one flexible leg and releases the at least one flexible leg from the drive member.

14. The method claim 13, wherein the syringe release gear is mounted to the rear side of the front plate by at least one syringe release cam pin.

15. The method of claim 14, wherein the at least one syringe release cam pin extends through the front plate.

16. The method of claim 13, wherein the syringe release gear includes an opening formed therein that is aligned with the syringe-receiving opening of the front plate.

17. The method of claim 16, wherein the opening in the syringe release gear includes a plurality of teeth formed around a circumference thereof.

* * * * *